(12) United States Patent
Goodstadt et al.

(10) Patent No.: US 11,099,089 B2
(45) Date of Patent: Aug. 24, 2021

(54) PORTABLE LOAD TESTING DEVICE

(71) Applicant: Drexel University, Philadelphia, PA (US)

(72) Inventors: Noel M. Goodstadt, Middletown, DE (US); Sheri P. Silfies, Wilmington, DE (US); Arun Ramakrishnan, Lansdowne, PA (US); Sriram Balasubramanian, Media, PA (US)

(73) Assignee: Drexel University, Philadelphia, PA (US)

( * ) Notice: Subject to any disclaimer, the term of this patent is extended or adjusted under 35 U.S.C. 154(b) by 319 days.

(21) Appl. No.: 16/073,657

(22) PCT Filed: Mar. 15, 2017

(86) PCT No.: PCT/US2017/022398
§ 371 (c)(1),
(2) Date: Jul. 27, 2018

(87) PCT Pub. No.: WO2017/160903
PCT Pub. Date: Sep. 21, 2017

(65) Prior Publication Data
US 2019/0033148 A1 Jan. 31, 2019

Related U.S. Application Data

(60) Provisional application No. 62/309,085, filed on Mar. 16, 2016, provisional application No. 62/423,261, filed on Nov. 17, 2016.

(51) Int. Cl.
*G01L 5/00* (2006.01)
*A63B 21/062* (2006.01)
(Continued)

(52) U.S. Cl.
CPC ............ *G01L 5/0004* (2013.01); *A61B 5/224* (2013.01); *A61B 5/6895* (2013.01);
(Continued)

(58) Field of Classification Search
CPC . A63B 21/063; A63B 21/0023; A63B 71/023; A63B 21/0628; A63B 5/224;
(Continued)

(56) References Cited

U.S. PATENT DOCUMENTS 4,607,841 A 8/1986 Gala
5,037,089 A * 8/1991 Spagnuolo ........... A63B 21/063
482/100

(Continued)

FOREIGN PATENT DOCUMENTS

GB 2483101 2/2012

OTHER PUBLICATIONS

International Search Report and Written Opinion for PCt/US2017/022398, dated Jun. 25, 2017. 10 pages.
(Continued)

*Primary Examiner* — Marrit Eyassu
(74) *Attorney, Agent, or Firm* — Joseph E. Maenner; Maenner & Associates, LLC

(57) ABSTRACT

In described embodiments, a strength testing device that can be applied to a weight stack is provided. The strength testing device can be used in physical therapy, chiropractics, or other rehabilitation professionals to assess the strength of a patient. The strength testing device can also be used in the fitness industry by strength coaches and personal trainers.

18 Claims, 10 Drawing Sheets

(51) Int. Cl.

| | |
|---|---|
| *A63B 21/002* | (2006.01) |
| *A63B 71/02* | (2006.01) |
| *A61B 5/22* | (2006.01) |
| *A61B 5/00* | (2006.01) |
| *A63B 24/00* | (2006.01) |
| *G01L 5/10* | (2020.01) |
| *A63B 71/06* | (2006.01) |

(52) U.S. Cl.
CPC ........ *A63B 21/0023* (2013.01); *A63B 21/063* (2015.10); *A63B 21/0628* (2015.10); *A63B 24/0062* (2013.01); *A63B 71/023* (2013.01); *G01L 5/10* (2013.01); *A61B 2562/0252* (2013.01); *A63B 2071/0627* (2013.01); *A63B 2210/50* (2013.01); *A63B 2220/17* (2013.01); *A63B 2220/40* (2013.01); *A63B 2220/51* (2013.01); *A63B 2220/833* (2013.01); *A63B 2225/20* (2013.01); *A63B 2225/50* (2013.01)

(58) Field of Classification Search
CPC .............. A63B 5/6895; A63B 24/0062; A63B 2225/20; A63B 2220/17; A63B 2071/0627; A63B 2210/50; A63B 2225/50; A63B 2220/40; A63B 2562/0252; A63B 2220/51; A63B 2220/833; G01L 5/0004; G01L 5/10

USPC ....................................................... 73/379.01
See application file for complete search history.

(56) References Cited

U.S. PATENT DOCUMENTS

| | | | |
|---|---|---|---|
| 5,088,727 A | | 2/1992 | Jones |
| 5,151,071 A | | 9/1992 | Jain et al. |
| 5,655,997 A | * | 8/1997 | Greenberg ........... A63B 21/063 |
| | | | 482/1 |
| 8,337,365 B2 | | 12/2012 | Kim et al. |
| 2005/0143228 A1 | * | 6/2005 | Lee .................... A63B 21/0628 |
| | | | 482/94 |
| 2006/0234842 A1 | * | 10/2006 | Minami ............. A63B 21/0628 |
| | | | 482/99 |
| 2013/0289448 A1 | | 10/2013 | Landry et al. |
| 2013/0345601 A1 | | 12/2013 | Bhugra et al. |
| 2014/0235409 A1 | * | 8/2014 | Salmon ............. A63B 21/0628 |
| | | | 482/8 |
| 2017/0197103 A1 | * | 7/2017 | Rau ....................... A63B 21/063 |
| 2018/0050234 A1 | * | 2/2018 | Kashyap ............. A63B 24/0075 |

OTHER PUBLICATIONS

Durfee, W.K. et al., "Rehabilitation and Muscle Testing", Encyclopedia of Medical Devices and Instrumentation, Second Edition. 2006. 10 pages.

* cited by examiner

PORTABLE LOAD TESTING DEVICE

CROSS-REFERENCE TO RELATED APPLICATION

The present application is a 371 of PCT Apolication PCT/US2017/022398, filed on Mar. 15, 2017, which claims the benefit of U.S. Provisional Patent Application 62/309,085, filed on Mar. 16, 2016, and U.S. Provisional Patent Application 62/423,261, filed on Nov. 17, 2016, all of which are incorporated herein by reference in their entireties.

BACKGROUND OF THE INVENTION

Field of the Invention

The present invention relates to a load and strength testing device that can be applied to a weight stack such as those commonly found in standard weight training machines (WTM).

Description of the Related Art

The demand for physical therapy services continues to grow as our population grows older, and access to healthcare improves. The Occupation Outlook Handbook from the Department of Labor and Statistics website projects growth by 36% through the year 2022 and projected revenues according to IBISWorld in 2015 will top 32 million dollars for physical therapy. In this same report, the author demonstrates how outpatient physical therapy services encompass more than 55% of the industry providing care to ~63% of the conditions treated within the industry. With the changes in healthcare leaning toward less reimbursement per patient, and more requirements for demonstrating quality care, it is imperative for clinicians to be able to demonstrate objective measures that quantify a patient's impairments and need for services. In the current health care environment, demonstrating a reliable, valid, and objective measurement of strength is a challenge for physical therapists. The most commonly used assessment tool for strength is the Manual Muscle Test (MMT) grading system from 0-5, with 0=absent and 5=normal, because it is fast and simple to perform. This technique utilizes observation and the use of the physical therapists hands to apply a manual resistance force to a patient attempting to move a body segment. Reliability of this method is poor and accuracy in grading is dependent on positioning of the patient and clinician, the clinician's strength and skill in applying the direction and force to the segment, and the reference used for normal. Adding a portable load cell, clinically referred to as a hand held dynamometer (HHD) such as manufactured by Lafayette or MicroFet, with a price range of $995-$1500, respectively, to this approach to strength testing, does not resolve the measurement reliability and accuracy issues. While an HHD can be quick to set up and simple to use, the clinician is still positioning and resisting the motion. Research has shown that significantly lower values for the quadriceps muscle strength are reported using this approach versus the gold standard isokinetic dynamometers. However, the gold standard, isokinetic dynamometer, a stand-alone system, is time consuming to set up and prohibitively expensive (~$45,000) to many clinical practices.

Within the health care promotion community, these approaches to strength testing are not typically utilized. Personal trainers and fitness professionals use single-repetition maximums to determine strength of their clients. This approach is too dangerous for most patients early in their rehabilitation, or for those deconditioned clients with chronic conditions. In addition, it can take a significant amount of testing time to reduce the factor of fatigue that affects this approach and the test results. Given that the goal from Exercise is Medicine®, is to get primary care physicians and other health care providers to include exercise as part of their treatment plans, more emphasis will be placed on personal trainers and fitness specialists to provide quality exercise prescriptions for a growing clientele with chronic health conditions like diabetes and heart disease.

Therefore, due to the lack of a high quality, portable, valid, and reliable strength testing techniques or devices, and the increasing need for objective data it is clear that there is a gap in the current clinical and fitness marketplace. It would be beneficial to provide an accurate, hands-free, and easily transportable device that mounts to exercise equipment already owned by most rehabilitation and fitness centers. Such a device should focus on demonstrating excellent validity and reliability for muscle strength testing currently used in evaluating patients in rehab post ACL reconstruction, knee and hip joint replacements or with patients suffering from knee and hip osteoarthritis. These represent situations where an accurate measure of muscle strength is imperative for quality clinical judgments.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a strength testing device that can be applied to a weight stack.

In another embodiment, the present invention is an isometric strength testing device comprising a vertical member, a sensor supported by the vertical member, and a pin receiver extending from the sensor. The pin receiver is adapted and configured to engage a pin such that the pin is further engageable with a hole in a vertical lifting bar of a weight stack machine. The sensor is adapted and configured to measure a force applied to the pin when the pin is inserted into the hole and a subject exerts force to the weight stack machine that is transferred to the vertical lifting bar.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
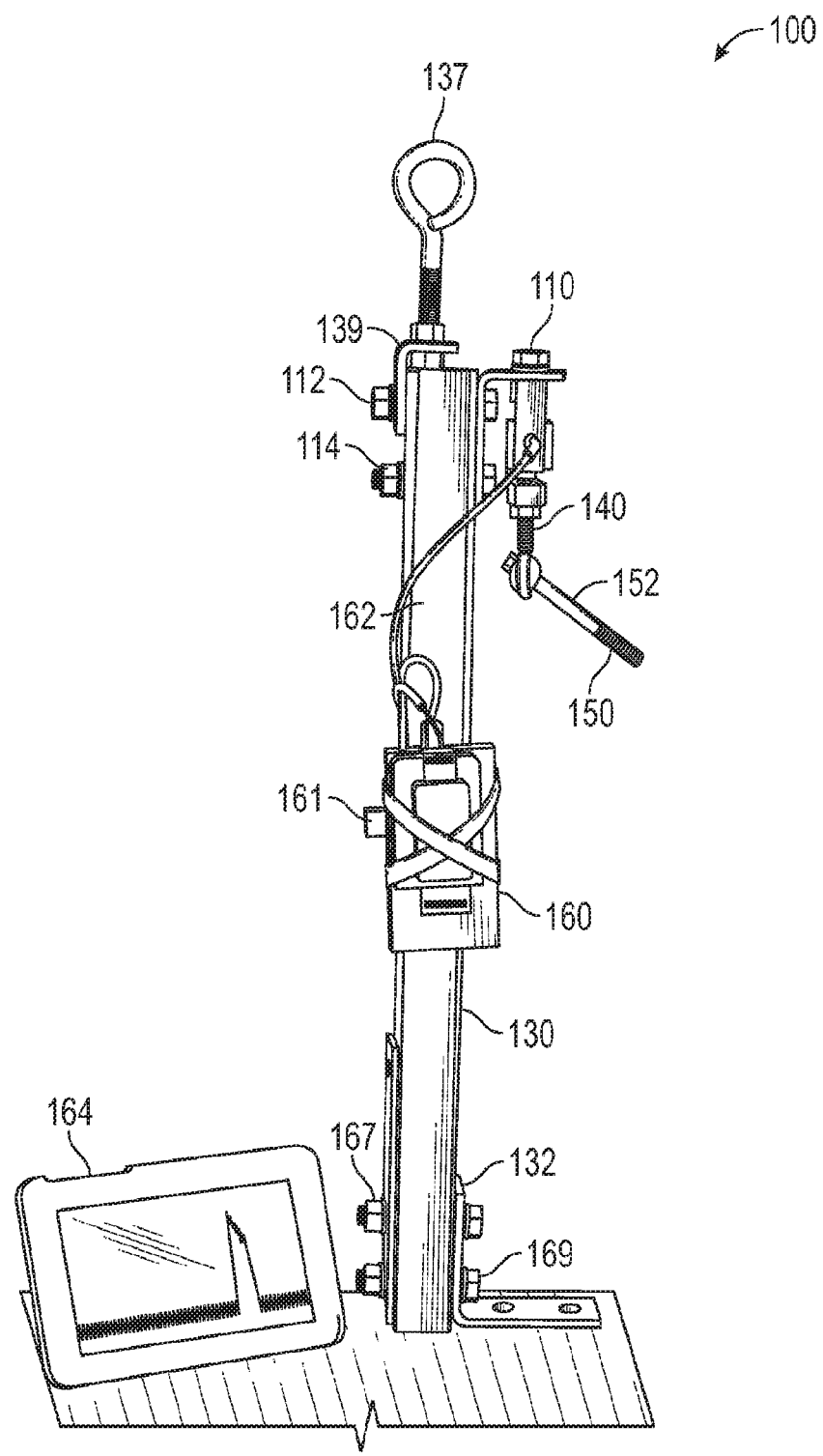
FIG. 1 is a side elevational view of a load and strength testing device according to a first exemplary embodiment of the present invention.

In the drawings, like numerals indicate like elements throughout. Certain terminology is used herein for convenience only and is not to be taken as a limitation on the present invention. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

Referring to FIGS. 1-6, a portable adaptable isometric strength testing device 100 ("device 100") according to an exemplary embodiment of the present invention is shown. Device 100 is used to provide an objective analysis of force applied to a weight stack, such as, for example, a quadriceps exercise machine. The inventive device has a modular design that allows swap/upgrade of parts to fit the application. These parts include swappable/replaceable load cells, end-clamps, extension rods, and other such parts.

Figure 2:
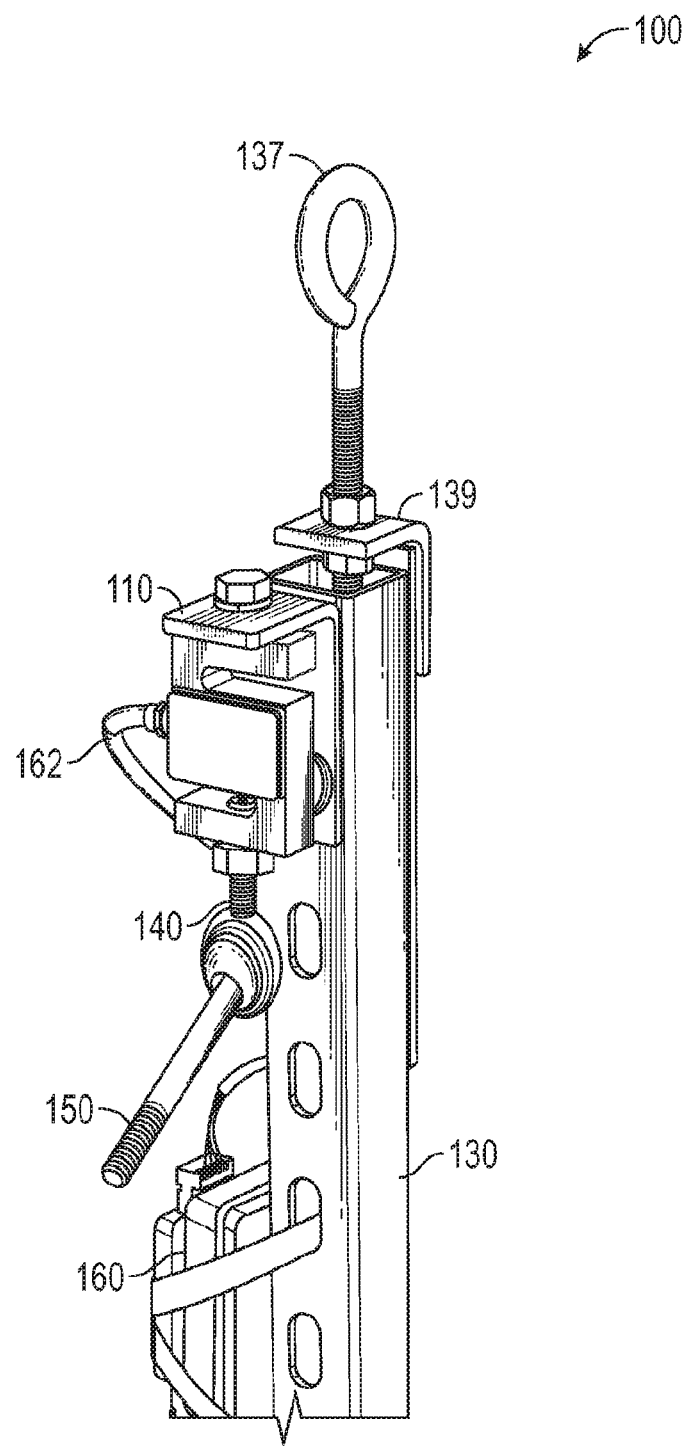
FIG. 2 is a perspective view of a top end of the device shown in FIG. 1.

Referring specifically to FIGS. 1 and 2, device 100 includes a load cell 110 that is attached to a vertical steel column 130 with a height adjustable base 132. Load cell 110 is electronically coupled to an amplified analog-to-digital converter 160, such as via an electrical cable 162. Converter 160 can be a 24 bit A/D converter that links to a peripheral device 164, such as, for example, an electronic pad, smartphone, tablets laptop, desktop, or other electronic device, either via an electrical cable (not shown) or wirelessly, such as by Bluetooth®, WiFi, or other suitable wireless connection. Converter 160 can be powered by a battery (not shown), which can be rechargeable and/or removable. The data sampling rate from load cell 110 can be between about 80 and about 100 samples per second. Peripheral device 164 can enable long term (>10 minutes) recording.

Optionally, a triaxial accelerometer 161 can be located with converter 160 to monitor the angular orientation of device 100 to assist an evaluator to determine the validity and accuracy of force measured with device 100. Accelerometer 161 can also be coupled to an audible alarm at recording device 164 that is activated to indicate that device 100 has tilted beyond a predetermined threshold. Such an alarm can avoid running trials with device 100 that result in improper and unusable data.

Figure 3:
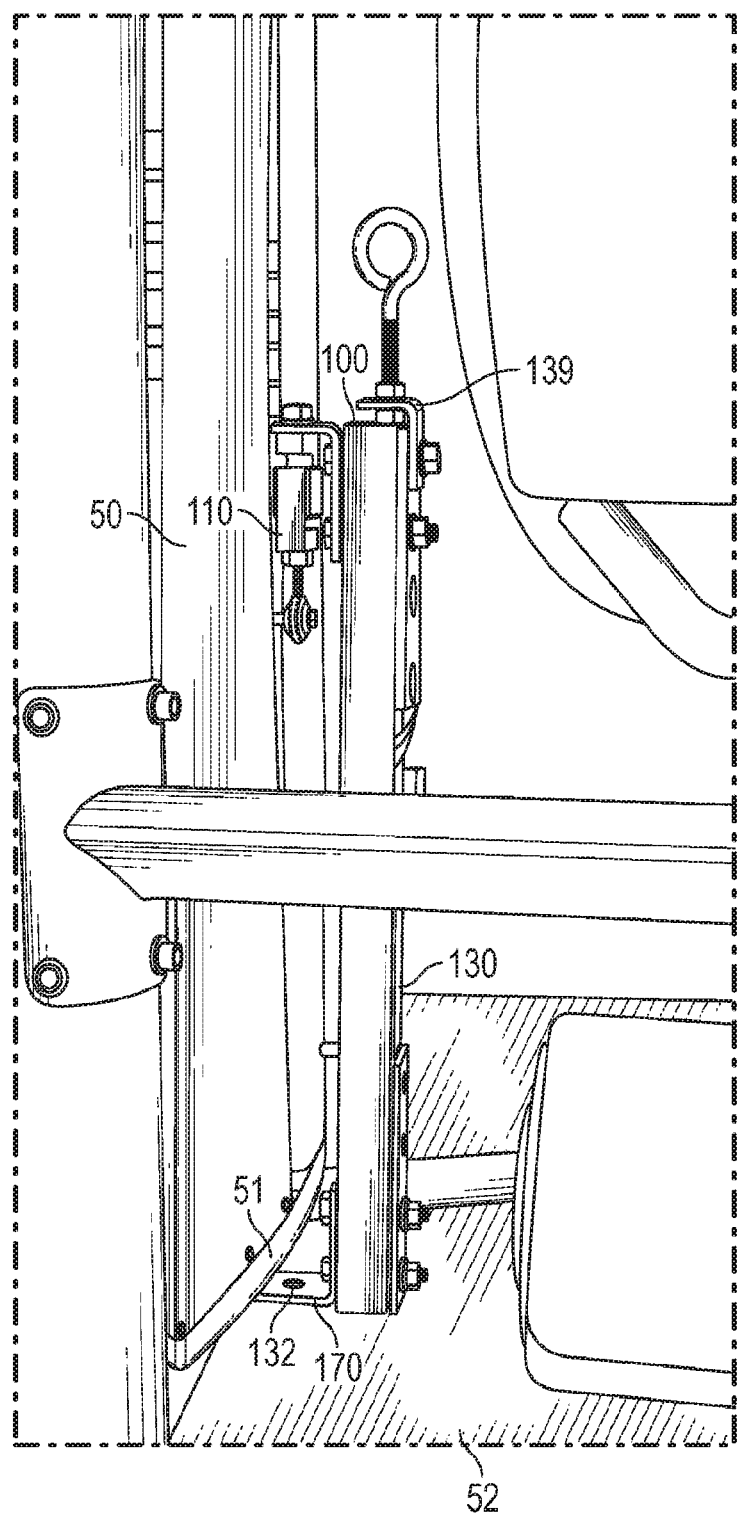
FIG. 3 is a side elevational view of the device shown in FIG. 1, attached to a weight stack.
Figure 5:
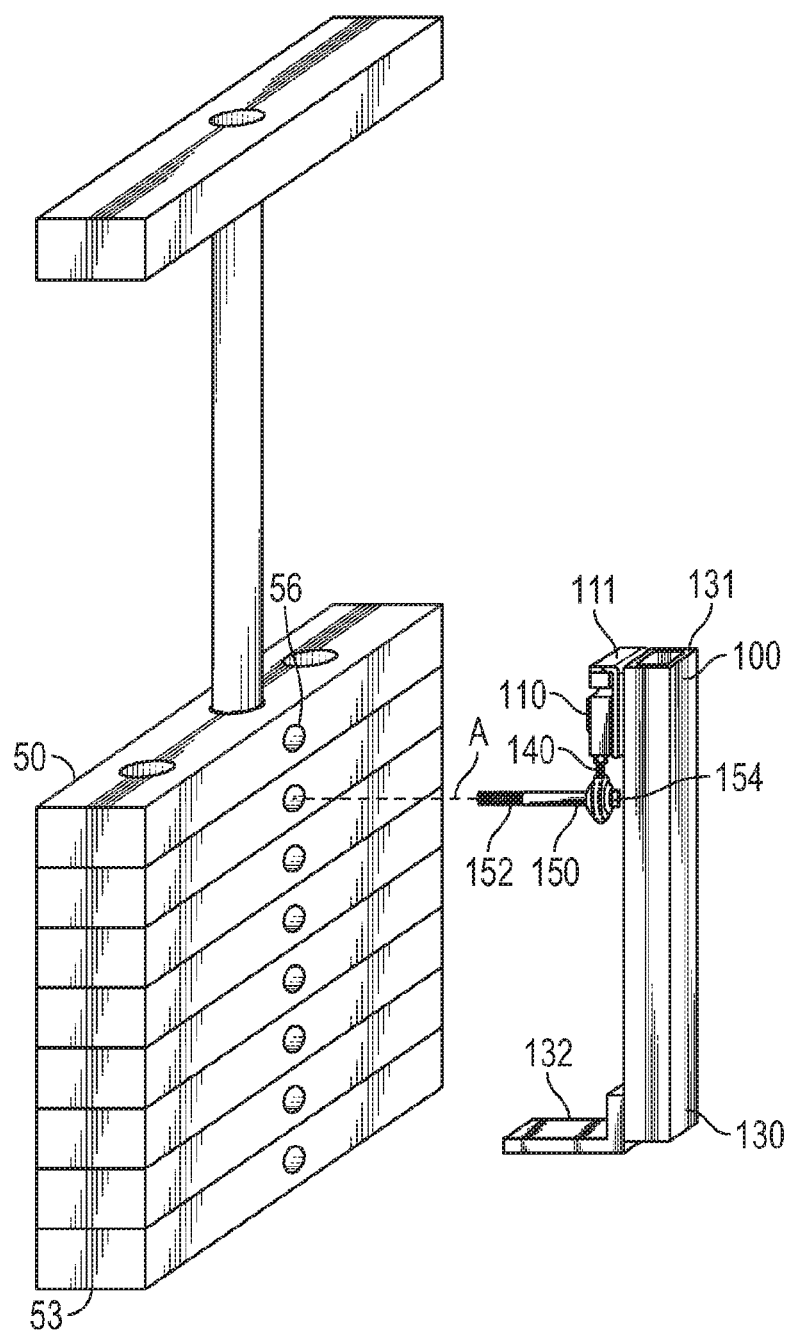
FIG. 5 is a perspective view of the device show in FIG. 1 being inserted into a weight stack.
Figure 6:
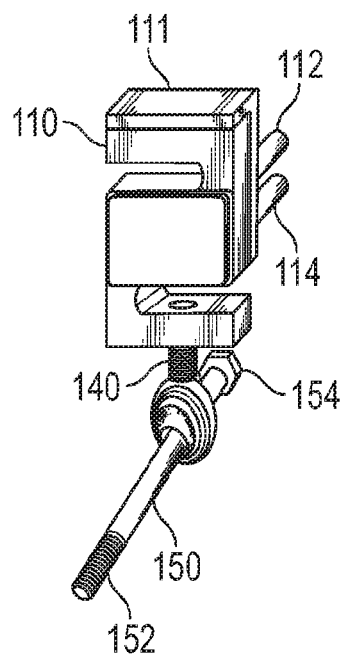
FIG. 6 is a perspective view of the load cell configuration used with the device shown in FIG. 1.

As shown in FIGS. 3 and 5, device 100 is connected to a standard weight training machine (WTM) 50 that utilizes a weight stack 53 for resistance.

Figure 4:
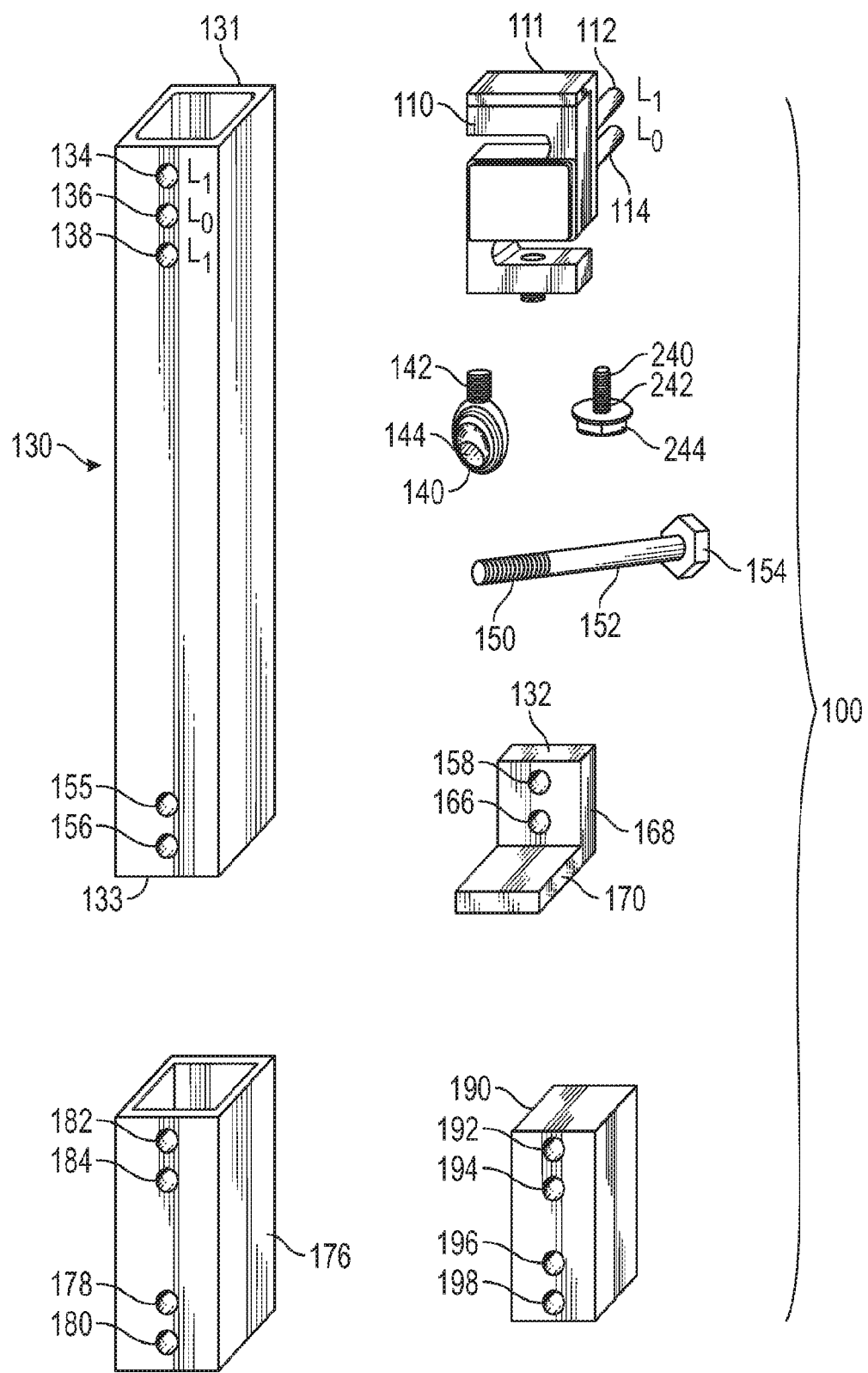
FIG. 4 is an exploded view of mechanical elements of the device shown in FIG. 1.

The mechanical elements of device 100 are shown in FIG. 4. Load cell 110 is an "S-beam" cell known in the art. Cell 110 is attached to an L-bracket 111 that includes a pair of parallel shafts, such as bolts, 112, 114, that extend outwardly from a rear wall of bracket 111. Shafts 112, 114 are used to releasably couple cell 110 to column 130 by inserting shafts 112, 114 into openings 134, 136, respectively, at the top end 131 of column 130.

A bottom portion of cell 110 includes a threaded opening (not shown) into which a threaded shaft 142 of a pin receiver, such as an eyebolt 140, is threaded. Eyebolt 140 includes an eye 144 into which the shaft 152 of a pin 150 is inserted. Pin 150 also includes a head 154 that is larger than the diameter of eye 144 so that, with shaft 152 of pin 150 inserted through eye 144, pin 150 can be retained within eyebolt 140. FIG. 5 shows cell 110 with bracket 111 and eyebolt 140 attached thereto, and pin 150 inserted through eyebolt 140. Eyebolt 140 is rotatable about load cell 110 to accommodate different configurations of WTM 50 to enable engagement of pin 150 with WTM 50.

Alternatively, instead of a separate eyebolt 140 and pin 150, a ball and socket joint can be used. Still alternatively, pin 150 can be supplied with device 100 or, alternatively, pin 150 can be the pin that is provided with WTM 50.

Referring to FIG. 4, column 130 is a hollow steel tube and includes openings 134, 136 for receiving shafts 112, 114 as discussed above. Those skilled in the art will recognize that column 130 can have a square, rectangular, circular, or other suitably shaped cross-section. Column 130 also includes an opening 138 located below opening 136 that is used to receive shaft 112 when load cell 100 is inverted, as will be described in more detail below with respect to device 200 according to the present invention.

As shown in FIGS. 1-3, a lifting eye 137 is threaded to an L-bracket 139, which is in turn threaded to top end 131 of column 130, on an opposing side of column 130 from load cell 110. Lifting eye 137 allows a clinician to pick up and move device 100 between different WTMs 50. Those skilled in the art will recognize that lifting eye 137 can be omitted and other lifting mechanisms can be provided.

Column 130 also includes openings 155, 156 at a bottom end 133 of column 130. Openings 155, 156 align with openings 158, 166 in a vertical portion of "L-shaped" base 132 to allow bolts 167, 169 (shown in FIG. 1) to be inserted through openings 155, 158 and 156, 166, respectively, to releasably secure base 132 to column 130.

Base 132 also includes a horizontal or base portion 170 extending outwardly from the bottom of vertical portion 168. Base portion 170 is used to engage bottom 51 of WTM 50 by engaging base portion 170 with bottom 51 of WTM 50, as shown in FIG. 3.

Optionally, if column 130 needs to be raised vertically to operate with a higher weight stack 53, an extension piece 176 can be releasably coupled to bottom 133 of column 130. Extension 176 includes openings 178, 180 at a bottom portion thereof that align with openings 158, 166 in base 132, as well as openings 182, 184 at a top portion thereof. If fine height adjustment is required eyebolt 140 can be rotated as required to perform such adjustment.

A coupler 190 can be used to releasably secure extension 176 to column 130. Coupler 190 includes openings 192, 194 that align with openings 155, 156 in bottom end 131 of column 130, as well as openings 196, 198 that align with openings 182, 184 in extension 176 such that bolts (not shown) can be inserted through openings 155, 192 and 156, 194 to secure column 130 to coupler 190 and bolts (not shown) can be inserted through openings 182, 196 and 184, 198, respectively, to couple extension 176 to column 130.

Bolts 167, 169 are inserted through openings 178, 158 and 180, 166, respectively, to bolt base 132 to extension 176.

To use device 100 on WTM 50, base 132 engages the bottom 51 of the stationary steel frame of WTM 50, as shown in FIG. 3. Referring to FIG. 5, at the top 131 of column 130, shaft 152 is slid into a slot 56 in a top plate 54 of a WTM 50 as shown by dashed line "A". Eye 144 through which shaft 152 is inserted acts as a bearing fulcrum such that shaft 152 rests just under the contact surface of cell 110. Device 100 essentially locks the weight stack 53 of the WTM 50 and thereby allows for measurement of isometric force via cell 110.

When force is applied to WTM 50 to lift weight stack 53, weight stack 53 applies a force to shaft 152, which in turn applies a force on load cell 110. Referring to FIG. 1, force on load cell 110 is translated into an electrical signal that is sent via electrical cable 162 from load cell 110 to amplified analog to digital converter 160 for further transmission to peripheral device 164 for visual/audio display, as well as data storage for later retrieval and analysis.

Device 164 and its associated software can include a "tare" function to correct for preloads, gain selection based on the pre-determined workout/device configuration, and a start/stop function for data collection. The gain can be adjusted based on whether the muscle group being tested is a large muscle group (e.g., quadriceps) or a small muscle group (e.g., infraspinatus). In an exemplary embodiment, the software can be developed using Matlab software, although those skilled in the art will recognize that other software can be used. Also, the software can be written to provide two-way communication between peripheral device 164 and load cell 110 to assist in calibrating load cell 110, adjusting tare and gain, as well as other processes, from peripheral device 164. The tare can be calculated directly from the software.

Raw data received from analog to digital converter 160 is filtered and analyzed to calculate, among other parameters, peak force output, energy expenditure, rate of force application, etc. These parameters, along with a graph of the applied force, are displayed (in real-time) to the clinician and/or patient/consumer to view and record. This data is saved locally on device 164 and can be exported for analysis and archival purposes. Device 164 is adapted to automatically begin recording the force values generated by load cell 110 when one of the force values exceeds a predetermined value. Additionally, device 164 can provide audible signals for the clinician and/or the patient to inform them about oncoming test landmarks, such as, for example, a specific number of repetitions, applied force, or other suitable information.

Figure 7:
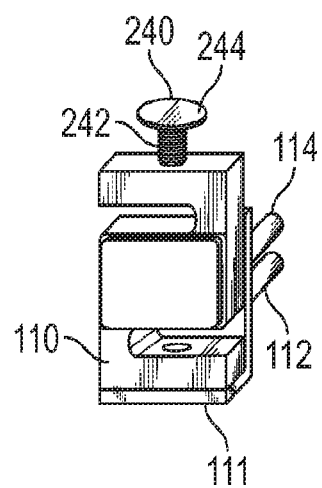
FIG. 7 is a perspective view of a load cell configuration used in a second exemplary embodiment of the present invention.
Figure 8:
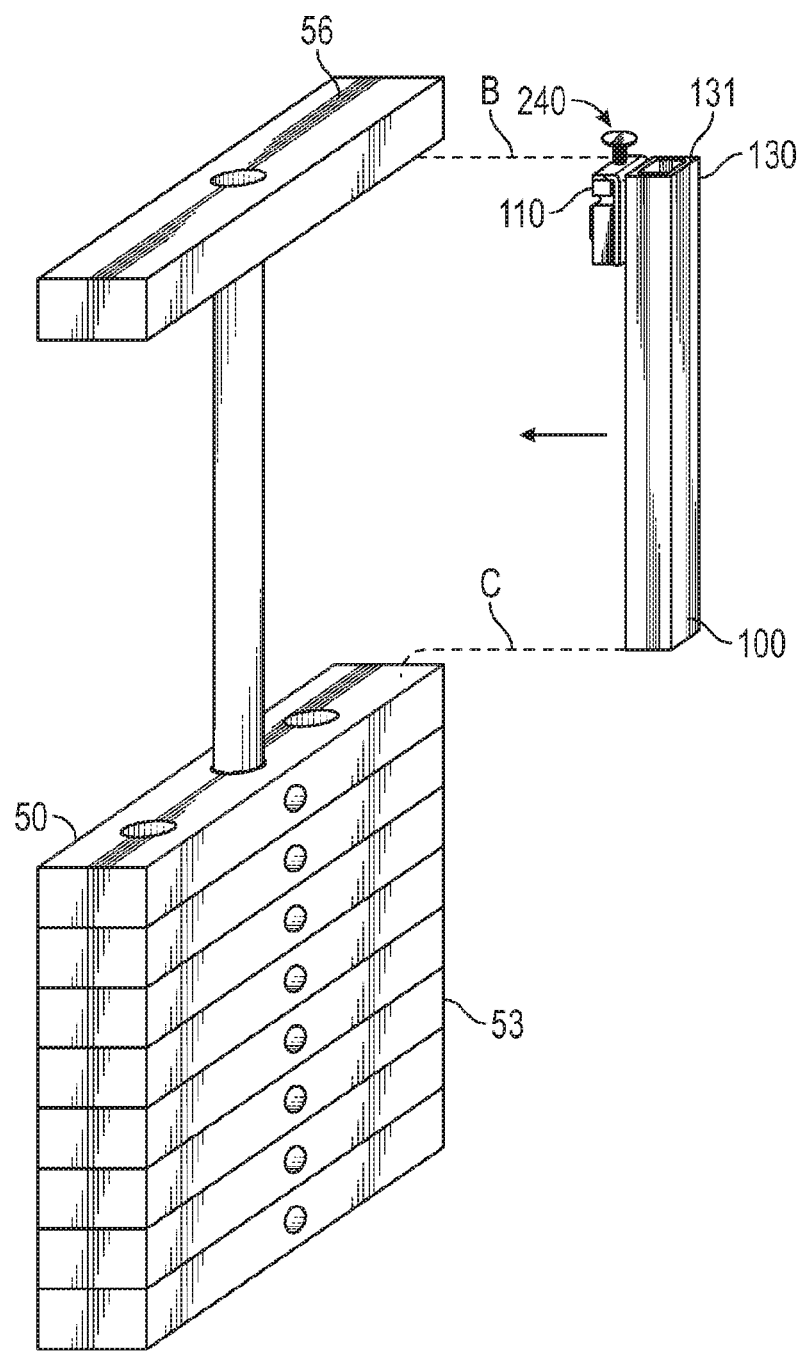
FIG. 8 is a perspective view showing the load cell configuration of FIG. 7 in a strength testing device according to a second exemplary embodiment of the present invention.

A portable adaptable isometric strength testing device 200 ("device 200") according to a second exemplary embodiment of the present invention is shown in FIGS. 7 and 8. This embodiment allows a clinician to essentially lock the weight stack 53 of the WTM 50 and thereby allow for measurement of isometric force.

Also, instead of eyebolt 140 being threaded to cell 110, eyebolt 140 is removed and replaced by bolt 240. Bolt 240 includes a threaded shaft 242 that is inserted by threading into cell 110 and a flat head 244 that is used to receive a compressive load from weight stack 53 as weight stack 53 is lifted upwardly during an exercise. FIG. 7 shows cell 110 with bracket 111 inverted such that bracket 111 is below cell 110 instead of on top of cell 110.

The modular design of devices 100/200 allows column 130 to be used with device 200. Shafts 112, 114 on bracket 111 are inserted into openings 138, 136 (shown in FIG. 4) on column 130. Base 132 from device 100 can be omitted for device 200.

Device 200 is applied to WTM 50 by placing the bottom 132 of column 130 on the top of the weight stack 53 as indicated by dashed line "C" and engaging load cell 110 with the top frame 56 of the WTM 50 as indicated by dashed line "B" in FIG. 8. Bolt 240 makes contact with the top frame 56 of WTM 50, while bottom 132 of column 130 sits on top of the weight stack 53. Device 200 can then be operated similarly to device 100 as described above.

Figure 9:
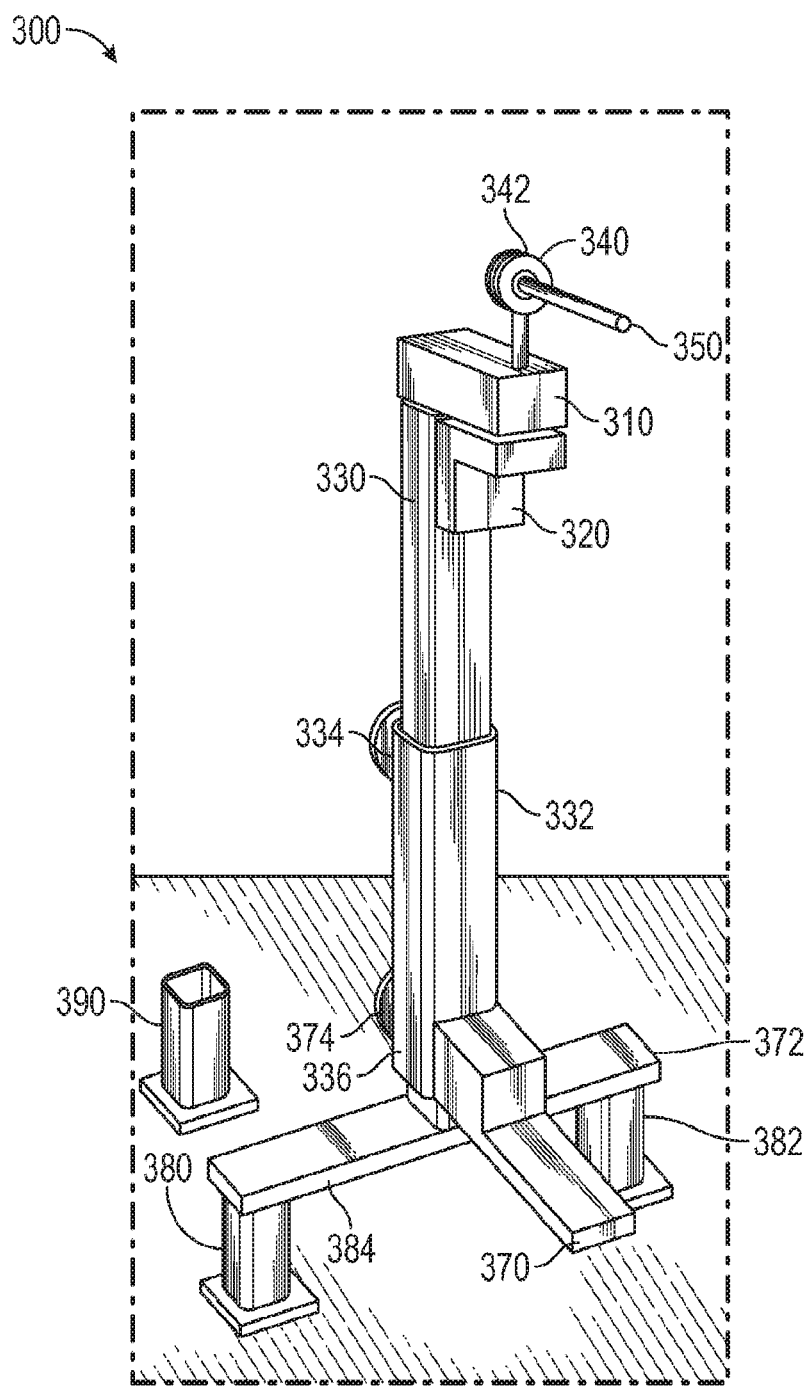
FIG. 9 is a front perspective view of a strength testing device according to a third exemplary embodiment of the present invention.
Figure 10:
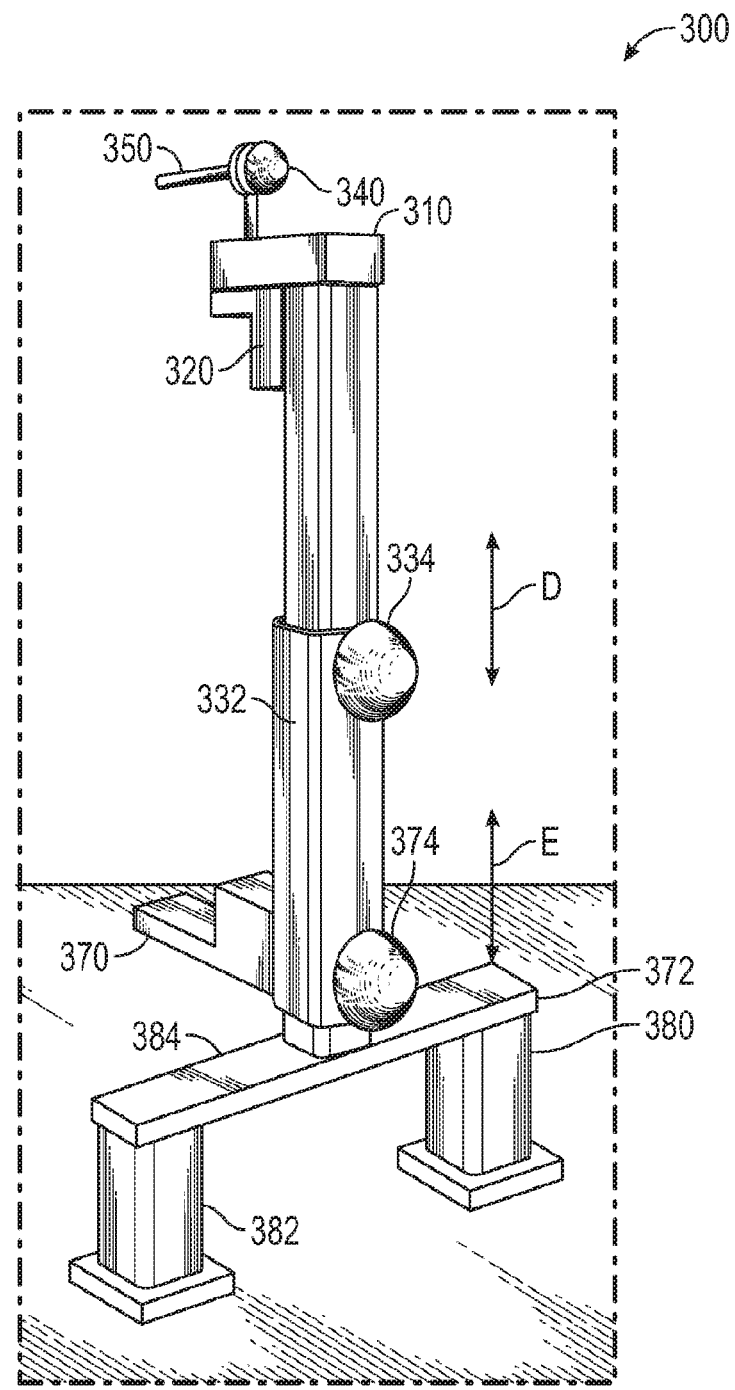
FIG. 10 is a rear perspective view of the strength testing device shown in FIG. 9.
Figure 11:
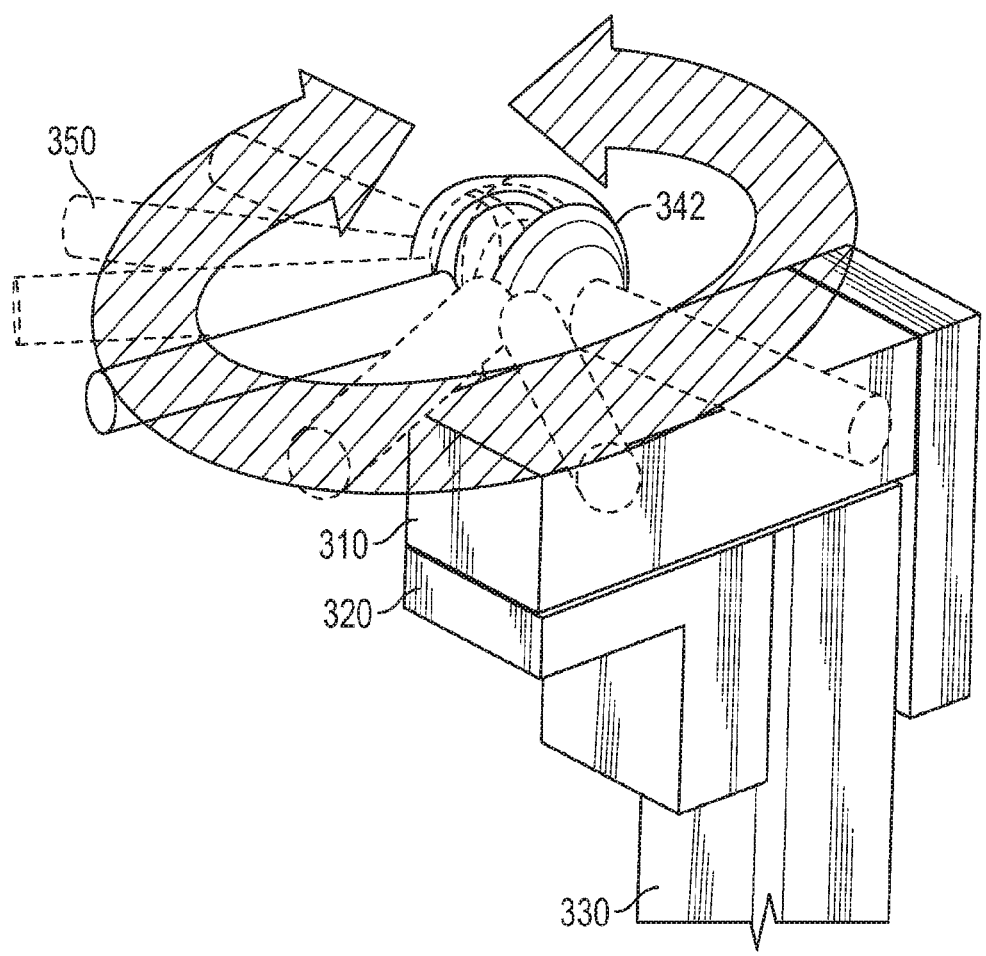
FIG. 11 is a perspective view of a top portion of the strength testing device shown in FIG. 9, demonstrating the ability of the pin support to rotate.

An alternative embodiment of a portable adaptable isometric strength testing device 300 ("device 300") according to another exemplary embodiment of the present invention is shown in FIGS. 9-11. Device 300 uses a cantilever load cell 310. Further, those skilled in the art will recognize that other shapes of load cells, such as S-shaped, cylindrical, cuboid, or other suitably shaped load cells can be used.

An eyebolt 340 extends upwardly from load cell 310 and a weight pin 350 extends through eye 342 of eyebolt 340. Pin 350 is inserted into top plate 54 of WTM 50 in a similar manner as pin 150 as described above. Weight pin 350 can be supplied with device 300 or, alternatively, weight pin 350 can be the pin that is provided with WTM 50. Referring to FIG. 11, eyebolt 340 is rotatable about load cell 310 to accommodate different configurations of WTM 50 to enable engagement of pin 350 with WTM 50.

Load cell 310 is mounted on a support 320 that is in turn connected to an upper vertical column 330. Upper vertical column 330 is telescopically inserted into a lower vertical column 332. A removable pin 334 allows for height adjustments of upper vertical column 330 with respect to lower vertical column 332, as shown by arrow "D" in FIG. 10.

A bottom end 336 of lower vertical column 332 includes a weight stack anchor 370 that is used to engage bottom 51 of WTM 50 by engaging weight stack anchor 370 with bottom 51 of WTM 50, similar to base portion 170, as shown in FIG. 3.

Bottom end 336 of lower vertical column 332 is hollow and allows for telescopic insertion of a support leg 372. A removable pin 374 allows for vertical height adjustments of lower vertical column 332 with respect to support leg 372, as shown by arrow "E" in FIG. 10. Support leg 372 can be used when WTM 50 has a support extension (not shown) that extends outwardly toward device 300. Support leg 372 includes first and second feet 380, 382 that are connected by a connecting portion 384. Connecting portion 384 straddles the WTM support extension such that feet 380, 382 are on either side of the support extension.

Support leg 372 is modular and removable from lower vertical column 332 for a WTM 50 that does not have the support extension discussed immediately above. In such cases, an alternative support foot 390 can be telescopically inserted into bottom end 336 of lower vertical column 332, making the support mechanism for lower vertical column 332 modular in FIG. 9.

It will be further understood that various changes in the details, materials, and arrangements of the parts which have been described and illustrated in order to explain the nature of this invention may be made by those skilled in the art without departing from the scope of the invention as expressed in the following claims.

We claim:

1. An isometric strength testing device comprising:
   a vertical member;
   a sensor supported by the vertical member;
   a pin receiver extending from the sensor; and
   a pin inserted into the pin receiver, the pin being engageable with a hole in a weight stack of a weight stack machine, wherein the pin restricts vertical upward movement of the weight stack,
   wherein the sensor is adapted and configured to measure a force applied to the pin when the pin is inserted into the hole and a subject exerts force to the weight stack machine that is transferred to the weight stack.

2. The isometric strength testing device of claim 1, wherein the orientation of the sensor is adjustable.

3. The isometric strength testing device of claim 1, wherein the pin receiver is in the vertical member.

4. The isometric strength testing device of claim 1, wherein the pin is mounted in a fulcrum located on an opposite side of the vertical member from the sensor.

5. The isometric strength testing device of claim 4 wherein the pin extends from the fulcrum through a slot in the vertical member.

6. The isometric strength testing device of claim 1, wherein the vertical member is a strut channel.

7. The isometric strength testing device of claim 1, wherein the sensor comprises a load cell.

8. The isometric strength testing device of claim 7, wherein the load cell comprises an "S-shaped load cell.

9. The isometric strength testing device of claim 7, wherein the load cell comprises a cantilever load cell.

10. The isometric strength testing device according to claim 1, wherein the vertical member has an adjustable height.

11. The isometric strength testing device according to claim 1, wherein the pin extends generally perpendicular to the vertical member.

12. The isometric strength testing device according to claim 1, wherein the sensor extends between the pin receiver and the vertical member.

13. The isometric strength testing device according to claim 1, further comprising a recording device electronically coupled to the sensor, wherein the recording device records force values transmitted from the sensor.

14. The isometric strength testing device according to claim 13, wherein the recording device is adapted to automatically begin recording the force values when one of the force values exceeds a predetermined value.

15. The isometric strength testing device according to claim 13, wherein the recording device is adapted to generate audible signals in anticipation of testing landmarks.

16. The isometric strength testing device according to claim 1, further comprising a horizontal member extending substantially perpendicularly from the vertical member and configured to engage with one of a bottom of a weight stack and a frame of a weight stack machine.

17. An isometric strength testing device for measuring the an amount of force applied to a weight stack in a weight stack machine, the testing device comprising:
   a vertical member having a top and a bottom; and
   a sensor supported by the top of the vertical member,
   wherein the sensor is configured to measure a force applied to the weight stack when the vertical member is inserted into the weight stack machine such that the bottom sits on top of the weight stack and the top engages a top frame of the weight stack machine, restricting movement of the weight stack toward the top frame.

18. An isometric strength testing device comprising:
   a vertical member;
   a sensor supported by the vertical member;
   a pin receiver extending from the sensor, the pin receiver adapted and configured to engage a pin such that the pin is further engageable with a hole in a vertical lifting bar of a weight stack machine;
   a pin inserted into the pin receiver, the pin being engageable with the hole in the vertical lifting bar of the weight stack machine, wherein the pin is supported by a fulcrum located on same side of the vertical member as the sensor; and
   an accelerometer electronically coupled to a recording device such that, if an angular orientation of the strength testing device exceeds a predetermined value, the recording device generates an audible signal,
   wherein the sensor is adapted and configured to measure a force applied to the pin when the pin is inserted into the hole and a subject exerts a force to the weight stack machine that is transferred to the vertical lifting bar.

* * * * *